(12) United States Patent
Gesualdo et al.

(10) Patent No.: US 12,036,201 B2
(45) Date of Patent: Jul. 16, 2024

(54) COMBINATION OF A UBIQUITIN-CONJUGATING ENZYME COMPLEX INHIBITOR AND ANTIHYPERTENSIVE AND/OR HYPOGLYCEMIC DRUGS IN DIABETIC KIDNEY DISEASE

(71) Applicant: UNIVERSITÀ DEGLI STUDI DI BARI ALDO MORO, Bari (IT)

(72) Inventors: Loreto Gesualdo, Altamura (IT); Paola Pontrelli, Bari (IT)

(73) Assignee: UNIVERSITÀ DEGLI STUDI DI BARI ALDO MORO, Bari (IT)

( * ) Notice: Subject to any disclaimer, the term of this patent is extended or adjusted under 35 U.S.C. 154(b) by 862 days.

(21) Appl. No.: 17/043,955

(22) PCT Filed: Mar. 28, 2019

(86) PCT No.: PCT/IB2019/052525
§ 371 (c)(1),
(2) Date: Sep. 30, 2020

(87) PCT Pub. No.: WO2019/186442
PCT Pub. Date: Oct. 3, 2019

(65) Prior Publication Data
US 2021/0015785 A1    Jan. 21, 2021

(30) Foreign Application Priority Data
Mar. 30, 2018    (IT) ............... 102018000004126

(51) Int. Cl.
*A61K 31/345*    (2006.01)
*A61K 31/277*    (2006.01)
(Continued)

(52) U.S. Cl.
CPC .......... *A61K 31/345* (2013.01); *A61K 31/277* (2013.01); *A61K 31/351* (2013.01);
(Continued)

(58) Field of Classification Search
None
See application file for complete search history.

(56) References Cited

FOREIGN PATENT DOCUMENTS

| WO | 2013123320 A1 | 8/2013 |
|----|---------------|--------|
| WO | 2014141295 A2 | 9/2014 |

(Continued)

OTHER PUBLICATIONS

Ahmadian et al., "Novel angiotensin receptor blocker, azilsartan induces oxidative stress and NFkB-mediated apoptosis in hepatocellular carcinoma cell line HepG2" Biomedicine and Pharmacotherapy vol. 99 pp. 939-946 (Year: 2018).*

(Continued)

*Primary Examiner* — Eric Olson
(74) *Attorney, Agent, or Firm* — Gregory P. Einhorn; Greer, Burns & Crain, Ltd.

(57) ABSTRACT

The present invention relates to a composition comprising at least one inhibitor of the enzymatic complex conjugating ubiquitin Ubc13/Uev1a and at least one anti-hypertensive agent inhibiting the renin-angiotensin-aldosterone system and/or a hypoglycemic agent. Medical uses and pharmaceutical compositions comprising this composition also fall within the scope of the present invention. In particular, this composition can be used for the treatment or prevention of the renal fibrotic damage, in particular in patients suffering from diabetes.

19 Claims, 7 Drawing Sheets

Figure 1:
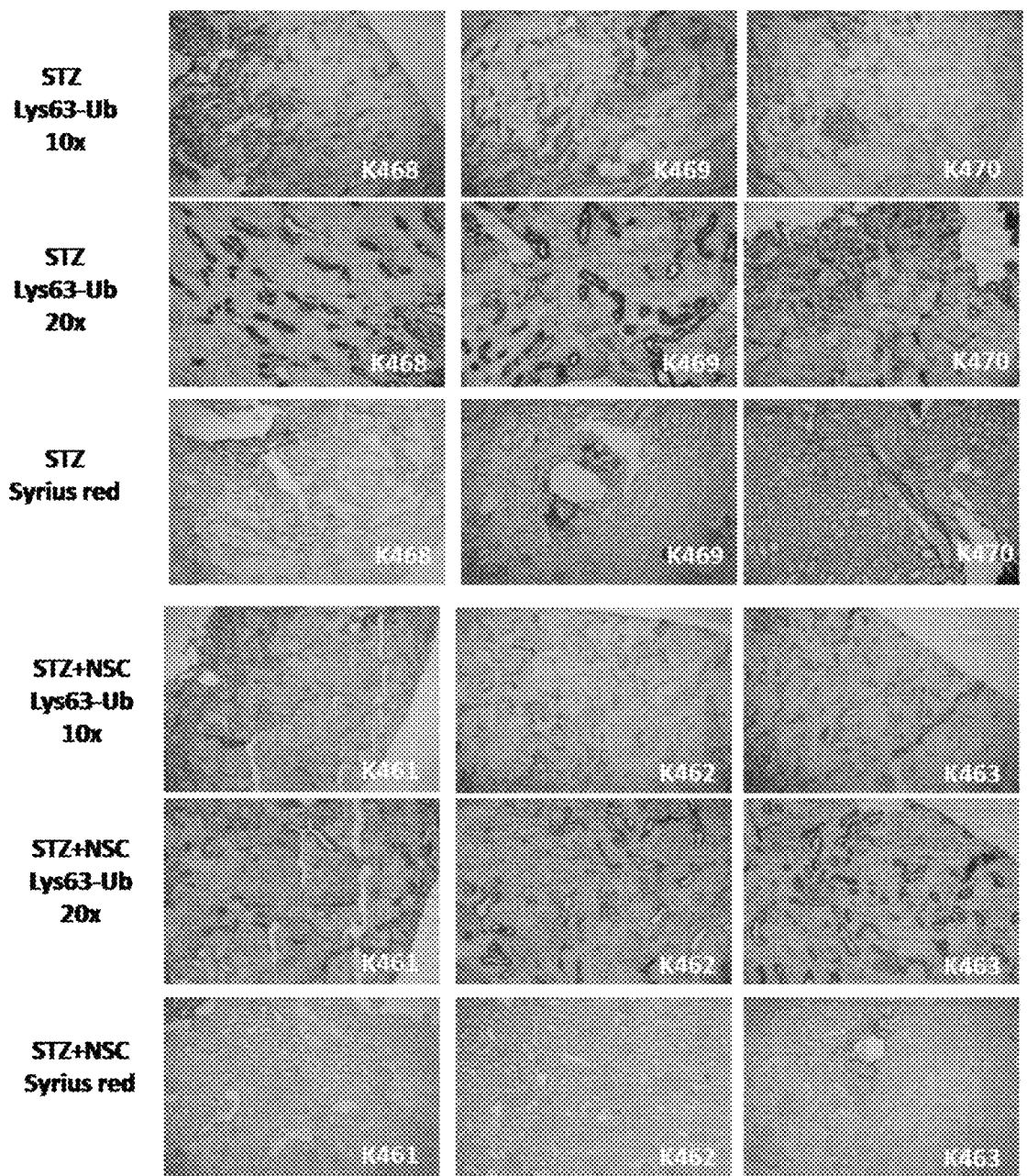

(51) Int. Cl.
  A61K 31/351 (2006.01)
  A61K 31/403 (2006.01)
  A61P 3/10 (2006.01)
  A61P 13/12 (2006.01)
(52) U.S. Cl.
  CPC .............. *A61K 31/403* (2013.01); *A61P 3/10* (2018.01); *A61P 13/12* (2018.01)

(56) References Cited

FOREIGN PATENT DOCUMENTS

| WO | WO-2018026673 A1 * | 2/2018 | ............ A61K 31/122 |
| WO | WO-2018081361 A1 * | 5/2018 | ......... A61K 31/4184 |

OTHER PUBLICATIONS

Tong et al., "Antagonistic effect of angiotensin II type 1 receptor blocker candesartan on angiotensin II-induced proliferation of primary acute myeloid leukemia cells" Zhongguo Bingli Shengli Zazhi vol. 27 No. 3 DOI 10.3969/j.issn.1000-4718.2011.03.018, English abstract (Year: 2011).*
Inigo et al., "Induction of apoptosis in leukemic cell lines treated with captopril, trandolapril and losartan: A new role in the treatment of leukaemia for these agents" Leukemia Research vol. 33 pp. 810-816 DOI 10.1016/j.leukres.2008.09.029 (Year: 2009).*
Kolati et al., "BAY 11-7082 ameliorates diabetic nephropathy byattenuating hyperglycemia-mediated oxidative stress and renal inflammation via NF-kB pathway" Environmental Toxicology and Pharmacology vol. 39 pp. 690-699 http://dx.doi.org/10.1016/j.etap.2015.01.019 (Year: 2015).*
Cortinovis et al., "Investigational drugs for diabetic nephropathy" Investigational drugs for diabetic nephropathy, Expert Opinion on Investigational Drugs, vol. 17 No. 10 pp. 1487-1500 DOI: 10.1517/13543784.17.10.1487 (Year: 2008).*
Bicket et al., "Using ACE Inhibitors Appropriately" American Family Physician vol. 66 No. 3 pp. 461-468 (Year: 2002).*
Liu et al., "Pharmaceutical Measures to Prevent Doxorubicin-Induced Cardiotoxicity" Mini-Reviews in Medicinal Chemistry vol. 17 pp. 44-50, DOI: 10.2174/1389557516666160621083659 (Year: 2017).*
Heart Outcomes Prevention Evaluation (HOPE) Study Investigators, "Effects of ramipril on cardiovascular and microvascular outcomes in people with diabetes mellitus: results of the HOPE study and MICRO-HOPE substudy" The Lancet vol. 355 pp. 253-259 (Year: 2000).*
Pontrelli et al., "Lysine 63 ubiquitination is involved in the progression of tubular damage in diabetic nephropathy" vol. 31 pp. 308-319 (Year: 2017).*
Ojima et al., "Empagliflozin, an Inhibitor of Sodium-Glucose Cotransporter 2 Exerts Anti-Inflammatory and Antifibrotic Effects on Experimental Diabetic Nephropathy Partly by Suppressing AGEs-Receptor" Endocrine Research vol. 47 pp. 686-692 DOI: 10.1055/s-0034-1395609 (Year: 2015).*
De Blasio et al., "The superoxide dismutase mimetic tempol blunts diabetes-induced upregulation of NADPH oxidase and endoplasmic reticulum stress in a rat model of diabetic nephropathy" European Journal of Pharmacology vol. 807 pp. 12-20, DOI: 10.1016/j.ejphar.2017.04.026 (Year: 2017).*
Koszegi et al., "P305—Renin-angiotensin-aldosterone system blockers in diabetic nephropathy: the role of epithelial to mesenchymal transition" Pediatric Nephrology vol. 27 p. 1783 (Year: 2012).*
Groma et al., "Demonstration of collagen type VI and alpha-smooth muscle actin in renal fibrotic injury in man" Nephrol Dial Transplant vol. 13 pp. 305-312 (Year: 1998).*
Pontrelli et al., "Lysine 63 ubiquitination is involved in the progression of tubular damage in diabetic nephropathy" The FASEB Journal, January, v31, n1, p. 308-319.
Amann et al., "ACE Inhibitors Improve Diabetic Nephropathy Through Suppression of Renal MCP-1" Diabetes Care, Aug. 2003, v 26, n 8, p. 2421-2425.
Bataillard et al., "Antihypertensive effect of an immunosuppressive agent, cyclophosphamide, in genetically hypertensive rats of the lyon strain" International Journal of Immunopharmacology, 1989, v 11, n 4, p. 377-384.
Bakhtiari et al., "Synergistic, cytotoxic and apoptotic activities of olmesartan with NF-kappa B inhibitor against HeLa human cell line" Toxicology Mechanisms and Methods, 2015, v 25, v 8, p. 614-621.
Tang et al., "Dapagliflozin slows the progression of the renal and liver fibrosis associated with type 2 diabetes" Am. Journal of Physiology: Endocrinology and Metabolism, 2017, v 313, n 5, p. E563-E576.
International Search Report and Written Opinion for PCT/IB2019/052525, Jul. 23, 2019.

* cited by examiner

COMBINATION OF A UBIQUITIN-CONJUGATING ENZYME COMPLEX INHIBITOR AND ANTIHYPERTENSIVE AND/OR HYPOGLYCEMIC DRUGS IN DIABETIC KIDNEY DISEASE

RELATED APPLICATIONS

This application is a national phase application claiming benefit of priority under 35 U.S.C. § 371 to International (PCT) Patent Application serial number PCT/IB2019/052525, filed Mar. 28, 2019, which claims benefit of priority to Italian Patent Application No. IT 102018000004126, filed Mar. 30, 2018. The aforementioned applications are expressly incorporated herein by reference in their entirety and for all purposes.

FIELD OF INVENTION

The present invention refers to the pharmaceutical field.

More specifically, it refers to the treatment of diabetic nephropathy, even more specifically to the prevention of fibrotic damage that occurs in said disease.

BACKGROUND OF THE INVENTION

Patients with diabetic nephropathy or patients with any chronic kidney disease, develop renal fibrosis over time.

Despite the financial and research investments spent to investigate the basic mechanisms of fibrosis, not much progress has been made in terms of therapeutic options currently available. (Anil Karihaloo. Curr Diab Rep (2012) 12:414-422).

Animal models have increased the understanding of the pathogenic mechanisms underlying the progression of renal damage such as diabetes complication.

However, no targeted therapies are still available especially to block fibrosis or slow down its progression.

Current therapies for the treatment of diabetes and its complications including diabetic nephropathy, encompass the use of various classes of drugs including drugs in the anti-hypertensive category, among whose drugs inhibitors of the renin angiotensin aldosterone system (RAAS), and hypoglycemic drugs, including metformin, dipeptidyl peptidase 4 inhibitors (DPP-4), sodium glucose transporter 2 inhibitors (SGLT-2) and GLP-1 receptor antagonists.

Blockade of angiotensin-converting enzyme or angiotensin II receptor induced by these antihypertensive drugs is able to slow down the progression of diabetic nephropathy, however the use of these molecules IS not sufficient to block the evolution of the disease (Mauer M, et al. N Engl J Med 361: 40-51, 2009).

Despite the widespread use of these drugs for the management of diabetes and hypertension, a large number of diabetic patients continues to develop renal damage and progress towards replacement treatment (dialysis or kidney transplantation).

Although it has been described that oral hypo-glycemic drugs have significant and long-term benefits on the kidney (Writing Team for the Diabetes C, Complications Trial/ Epidemiology of Diabetes I, Complications Research G. Sustained effect of intensive treatment of type 1 diabetes mellitus on development and progression of diabetic nephropathy: the Epidemiology of Diabetes Interventions and Complications (EDIC) study. JAMA. 2003; 290(16):2159-67), however such drugs can promote the risk to increase severe hypoglycemia and mortality related to the cardiovascular disease in diabetic patients.

For example, the ability of SGLT2 receptor inhibitors to reduce hyper-filtration and glomerular sclerosis has been demonstrated in various experimental models of Diabetic Nephropathy; however, these inhibitors are able to modulate only some of the typical molecular and histological markers of fibrosis.

Molecular processes specifically regulated by SGLT2 receptor inhibitors need more investigation in order to improve the therapeutic regimen of patients with Diabetic nephropathy.

Metformin, an oral hypoglycemic drug used in the treatment of diabetes, is a known activator of the activated protein kinase AMP (AMPK), which influences the cellular energy metabolism: although it has been demonstrated that metformin inhibits organ fibrosis (Feng Y, Wang S, Zhang Y, Xiao H. Metformin attenuates renal fibrosis in both AMPKα2-dependent and independent manners. Clin Exp Pharmacol Physiol. 2017; 44(6):648-655; Shen Y, Miao N, Xu J, Gan X, Xu D, Zhou L, Xue H, Zhang W, Lu L. Metformin Prevents Renal Fibrosis in Mice with Unilateral Ureteral Obstruction and Inhibits Ang II-Induced ECM Production in Renal Fibroblasts. Int J Mol Sci. 2016; 17(2)), the antifibrotic mechanism of action is still not clear. Finally, glucagon-like peptide-1 (GLP-1) analogues, belonging to the class of incretino-mimetic drugs that carry out their hypoglycemic action by stimulating insulin production by beta-pancreatic cells, although showing promising results in several animal and cellular models (Li Y K, Ma D X, Wang Z M, Hu X F, Li S L, Tian H Z, Wang M J, Shu Y W, Yang J. The glucagon-like peptide-1 (GLP-1) analog liraglutide attenuates renal fibrosis. Pharmacol Res. 2018. pii:S1043-6618(17)31160-X; Bisgaard L S, Bosteen M H, Fink L N, Sorensen C M, Rosendahl A, Mogensen C K, Rasmussen S E, Rolin B, Nielsen L B, Pedersen T X. Liraglutide Reduces Both Atherosclerosis and Kidney Inflammation in Moderately Uremic LDLr–/– Mice. PLoS One. 25 2016; 11(12): e0168396), don't seem to improve kidney function (Marso S P, Daniels G H, Brown-Frandsen K, Kristensen P, Mann J F, Nauck M A, et al. Liraglutide and Cardiovascular Outcomes in Type 2 Diabetes. N Engl J Med. 2016; 375(4): 311-22).

New molecules acting on target mechanisms, such as glomerular hyperfiltration, inflammation and fibrosis are therefore highly desired to facilitate the development of new effective treatments (Alicic R Z, Rooney M T, Tuttle K R. Clin J Am Soc Nephrol.; 12(12): 2032-2045, 2017). Thus, novel pharmacological therapies are needed to slow down or block the progression of diabetic nephropathy and in particularly the development of the renal fibrotic damage.

Over the last years, the importance of ubiquitination in diabetic nephropathy significantly growing (Huang W et al. Biomed Res Int. 2014; 2014:684765; Gao C, et al. Biomed Res Int. 2014; 2014:160692; Gao C, et al. J Diabetes Res. 2014; 2014:918396; Goru S K, Kadakol A, Gaikwad A B. Pharmacol Res. 2017; 120:170-179; Pontrelli P. et al. Minerva Med. 2018).

The accumulation of Lysine 63 ubiquitinated proteins has been described from the inventors of the present invention as a mechanism potentially involved in the progression of the fibrotic damage in diabetic patients, linked to the increased expression of the UBE2v1 gene (Pontrelli P, et al. FASEB J.; 31: 308-319, 2017). The described results have demonstrated that this mechanism affects only renal tubular cells and induces a "cellular transformation" that is epithelial-to-mesenchymal transition, which induces tubular cells to produce fibrotic matrix. It has also been demonstrated that the NSC697923 compound, a Ubc13-Uev1A E2 complex inhibitor, by specifically inhibiting the accumulation of lysine 63 ubiquitinated proteins, blocks the epithelial to mesenchymal transition in an in vitro cellular model of immortalized human renal tubular cells HK2.

However, no evidence has been described regarding the role of the inhibition of lysine 63 ubiquitination in blocking the onset or the progression of the fibrotic renal damage linked to diabetic kidney disease in vivo. In fact there is no experimental data on animal models showing that inhibition of this mechanism can have a real effect on the renal fibrotic damage.

The use of the enzymatic complex UBC13/Uev1A inhibitors has been described for the treatment of some diseases, in particular for the treatment of cancer. See as example the following patents: WO2013123320 describes the use of the NSC697923 inhibitor for the treatment of B cells malignancies; US2002173524 describes the use of a molecule similar to the NSC697923 inhibitor for some CCR4 mediated complications including type I diabetes.

The international patent application, publication n. WO 2013/123320, describes the treatment of B cell malignancies via administration of 2-(4-methylphenyl)sulfonyl-5-nitrofuran in combination with cyclophosphamide. Cyclophosphamide has been described as an anti-hypertensive drug, however cyclophosphamide is well known to act on T cells, thus its anti-hypertensive effect is linked to an increased lymphopenia with no effect on the renin-angiotensin-aldosterone system (Bataillard A. et al., 1989, Antihypertensive effect of an immunosoppresive agent, cyclophosphamide, in genetically hypertensive rats of the lyon strain"); in fact, in clinical practice, cyclophosphamide is not used for the treatment of hypertension.

The international patent application, publication n. WO2014/141295 describes the use of the renin-angiotensin-aldosterone system inhibitors in combination with hydroxychloroquine to treat diabetic nephropathy.

The use of the inhibitors of the renin-angiotensin-aldosterone system is known for the treatment of diabetic nephropathy (Amman B. et al., 2003, ACE Inhibitors Improve Diabetic Nephropathy Through Suppression of Renal MCP-1, Diabetes Care, 26(8), 2421-2425).

However, in the state of the art it has not been described the use of NSC697923 or similar inhibitors for the treatment of fibrotic complications of diabetic nephropathy, neither alone nor in combination with other drugs.

It remains in the state of the art the need of a pharmacological therapy for diabetic nephropathy able in particular to slow down or effectively block the progression of the fibrotic damage or to prevent its onset.

It has now been found that a combination of the NSC697923 inhibitor with a compound inhibitor of the renin-angiotensin-aldosterone system having antihypertensive effects, or with an hypoglycemic compound, is able to reduce both the development of renal fibrosis and albuminuria in renal damage.

In particular, it has been found that a combination of the NSC697923 inhibitor with either an ACE-inhibitor (angiotensin converting enzyme inhibitor) or an hypoglycemic compound inhibitor of the sodium/glucose cotransporter 2 (SGLT2) receptor, reduces hyperglycemia-induced epithelial to mesenchymal transition in vitro and the degree of tubule-interstitial fibrosis in vivo in a mouse model of renal damage induced by diabetes.

Moreover it has been found that this combination, in particular the association between NSC697923 and an ACE-inhibitor, significantly reduces albuminuria in diabetic mice (STZ), more than single drug administration. Albuminuria is the loss of albumin in urines that characterizes the first steps in the development of diabetic nephropathy and that, in the absence of an effective treatment, can lead to the complete loss of renal function. Albuminuria first and proteinuria later, can have a direct role in the progression of end stage renal disease since they can promote a tubular-interstitial injury.

Such a composition has therefore the advantage of being effective in reducing both albuminuria and the fibrotic damage at the same time, thanks to the combined action of the two compounds that leads to an overall improvement of renal function and a consequent reduced risk for the patient to develop chronic renal failure, treatable with renal replacement therapy (dialysis or kidney transplant).

SUMMARY OF THE INVENTION

It is an object of the present invention a composition comprising at least one inhibitor of the enzymatic ubiquitin-conjugating complex UBC13/Uev1A and at least one anti-hypertensive drug inhibitor of the renin-angiotensin-aldosterone system and/or an hypoglycemic drug.

Preferably, said inhibitor of the enzymatic ubiquitin-conjugating complex UBC13/Uev1A is the 2-(4-methylphenyl)sulfonyl-5-nitrofuran compound, known as NSC697923.

Preferably, said anti-hypertensive drug is an inhibitor of the renin-angiotensin-aldosterone system.

Preferably, the inhibitor of the renin-angiotensin-aldosterone system is an (ACE) inhibitor, in particular the compound Ramipril, or an angiotensin II receptor antagonist.

Preferably, said hypoglycemic drug is selected in the group consisting of alpha-glucosidase inhibitors, amylin analogues, dipeptidyl peptidase 4 inhibitors, incretin mimetics, insulin, meglitinides, non-sulfonylureas, 2 sodium glucose (SGLT2) co-transporter inhibitors, sulfonylureas, thiazolidinediones, and combinations thereof.

Falls within the scope of the present invention said composition for use as a medicament.

In particular, it is an object of the present invention, said composition for the treatment, in particular in the early treatment, and/or in the prevention of the renal fibrosis.

The early treatment may in particular have the purpose to prevent the onset of fibrosis.

More specifically, said composition is for use for the prevention of fibrosis and of the progression of renal fibrosis.

Said renal fibrosis may be subsequent to any chronic renal disease. May also be subsequent to diabetic nephropathy.

More in particular, it is an object of the present invention said composition for use for the treatment, in particular early treatment, and/or in the prevention of renal fibrosis that occurs in diabetic nephropathy.

In one embodiment, said composition is for use in the treatment, in particular early treatment, and/or in the prevention of diabetic nephropathy.

Even more particularly, said composition is for the administration to a diabetic patient. Said diabetic patient can be normo-albuminuric, micro-albuminuric, or macro-albuminuric. He can have unaltered renal function or can be a diabetic patient with diabetic nephropathy.

It is also an object of the present invention a pharmaceutical composition comprising as active ingredients at least one inhibitor of the enzymatic ubiquitin-conjugating complex UBC13/Uev1A and at least one anti-hypertensive drug, for example an inhibitor of the renin-angiotensin-aldosterone system, and/or an hypoglycemic drug, for example alpha-glucosidase inhibitors, amylin analogues, dipeptidyl peptidase 4 inhibitors, incretin mimetics, insulin, meglitinides, non-sulfonylureas, 2 sodium glucose (SGLT2) cotransporter inhibitors, sulfonylureas, thiazolidinediones, and combinations thereof, together with at least one pharmaceutically acceptable vehicle and/or excipient.

It has been found in fact that the inhibitor of the enzymatic complex UBC13/Uev1A, NSC697923, reduces significantly tubular-interstitial fibrosis in diabetic animals, and in combination with an ACE-inhibitor (ramipril), reduces in vitro the hyperglycemia-induced epithelial-to-mesenchymal transition in tubular cells and therefore the fibrotic damage, while ACE-inhibitors alone have no effect on the progression of fibrosis.

Moreover, the association between the two compounds significantly acts on albuminuria reduction, an important clinical feature in diabetic nephropathy and in other chronic renal diseases.

The two compounds can than be advantageously used together to reduce and/or block the progression of the fibrotic damage present in diabetic nephropathy or in other chronic kidney diseases.

Moreover, it has been found that the inhibitor of the enzymatic complex UBC13/Uev1A, NSC697923, together with the SGLT2 receptor inhibitor, empaglifozin, significantly and synergistically reduce the hyperglycemia-induced epithelial-to-mesenchymal transition in tubular cells and then finally the progression of kidney fibrosis.

DETAILED DESCRIPTION OF THE INVENTION

Definitions

Within the meaning of the present invention, "inhibitor of the enzymatic ubiquitin-conjugating complex UBC13/Uev" means a compound that inhibits appreciably the activity of the enzymatic ubiquitin-conjugating complex UBC13/Uev, also known as Ubc13/UBE2v1 complex.

Within the meaning of the present invention, "agent with anti-hypertensive action" or "anti-hypertensive agent" means a compound that reduces blood pressure, in particular it refers to a drug used to treat blood pressure diseases, in particular it refers to an inhibitor of the renin-angiotensin-aldosterone system.

Within the meaning of the present invention, "inhibitor of the renin-angiotensin-aldosterone system" refers to a compound that inhibits the renin-angiotensin-aldosterone system behavior. This inhibition can occur at any level and on any element or mechanism of the system. In particular, the inhibitor can act on any passage of the aforesaid system. In particular can act on angiotensin II production or on its receptors. "Renin-angiotensin system" is here used as a synonym for "renin-angiotensin-aldosterone system".

Within the meaning of the present invention, "ACE-inhibitors" refers to any compound that inhibits the angiotensin converting enzyme.

Within the meaning of the present invention, "agent with hypoglycemic action" or "hypoglycemic agent" refers to a compound that reduces glucose concentration in the blood. In particular, it refers to a drug commonly used to induce a reduction in glycemia.

Within the meaning of the present invention, "diabetic nephropathy" means a disease that occurs in diabetic patients characterized by altered renal function, with albuminuria and typical renal damage (Tervaert T W, et al. (2010) J Am Soc Nephrol.; 21(4): 556-563).

Within the meaning of the present invention, "renal fibrosis" means a clinical condition characterized by an abnormal increase in the kidney of the connective components versus parenchymal ones. "Fibrotic renal damage" is here used as a synonym.

Within the meaning of the present invention, "prevention" means the risk reduction of the onset and development of a disease.

Within the meaning of the present invention, "prevention of progression" means an administration to a patient with the aim to block or slow the progression of a disease.

Within the meaning of the present invention, "early treatment" refers to an administration to a patient in an early stage of the disease, for example in a stage where the first signs and symptoms of the disease begin to show.

Within the meaning of the present invention, "normo-albuminuric patient" refers to a patient with urinary albumin excretion in the 24 h below 30 mg.

Within the meaning of the present invention, "micro-albuminuric patient" refers to a patient with urinary albumin excretion in the 24 h between 30 mg and 300 mg.

Within the meaning of the present invention, "macro-albuminuric patient" refers to a patient with urinary albumin excretion in the 24 h greater than 300 mg.

FIGURES

FIG. 1. NSC697923 (NSC) effect on Lysine 63 ubiquitinated proteins (Lys63-Ub) accumulation and on tubular-interstitial fibrosis (assessed by Sirius red staining) in diabetic mice kidneys (STZ). Letters and numbers in the figure indicate animals represented in the figure.

Figure 2:
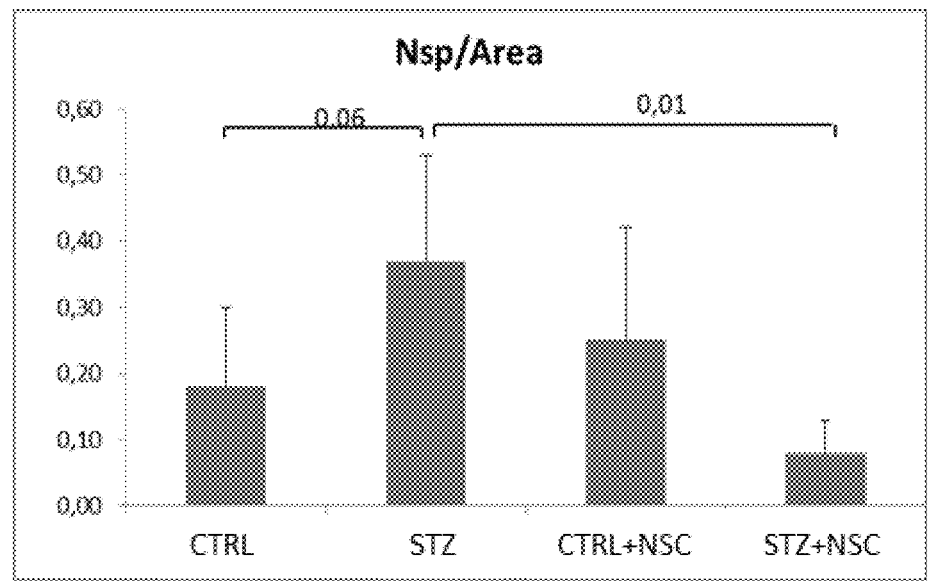

FIG. 2. Quantization of renal fibrosis assessed by Sirius red staining in kidneys of normal mice (CTRL) and diabetic mice (STZ) treated with or without NSC697923 (NSC). Quantification is reported as a number of strongly positive cells (NSP: number of strong positive cells) per unit area.

Figure 3:
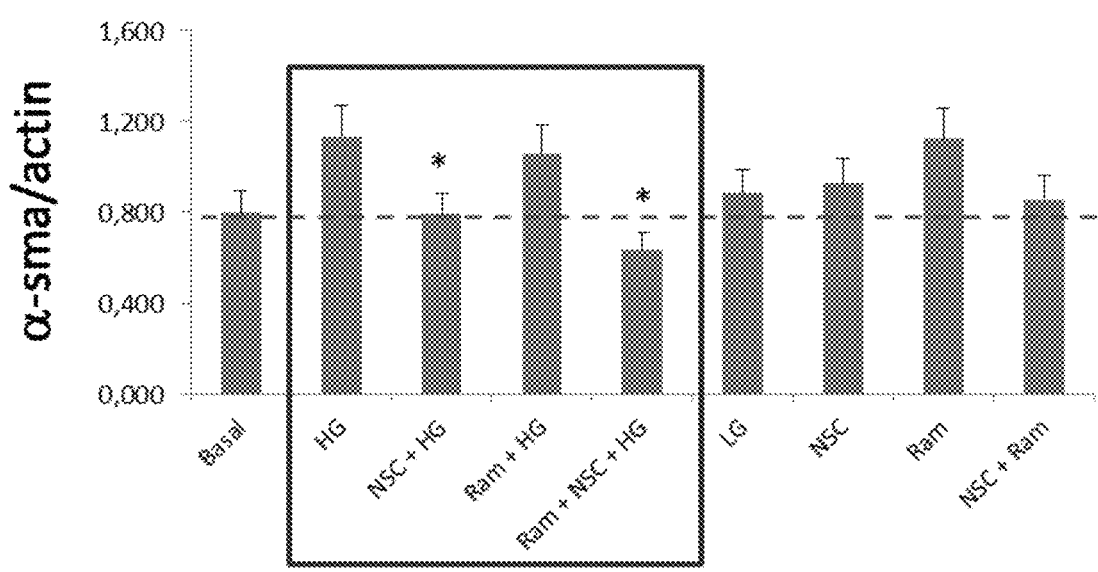

FIG. 3. Western blotting on renal tubular cells HK2 to evaluate α-sma expression (normalized to actin expression) in the presence of high glucose (HG), NSC697923 (NSC), Ramipril (Ram), L-glucose (LG), alone or in association. *p<0.05 vs HG FIG. 4. Quantization of α-sma expression (a) and Lysine 63 ubiquitinated proteins (b) evaluated by confocal microscopy on immortalized renal tubular cells (HK2) in the presence of NSC697923 (NSC), Ramipril (Ram) under high glucose conditions (HG) or basal. Quantification is reported as signal intensity in percentage of Area.

Figure 5:
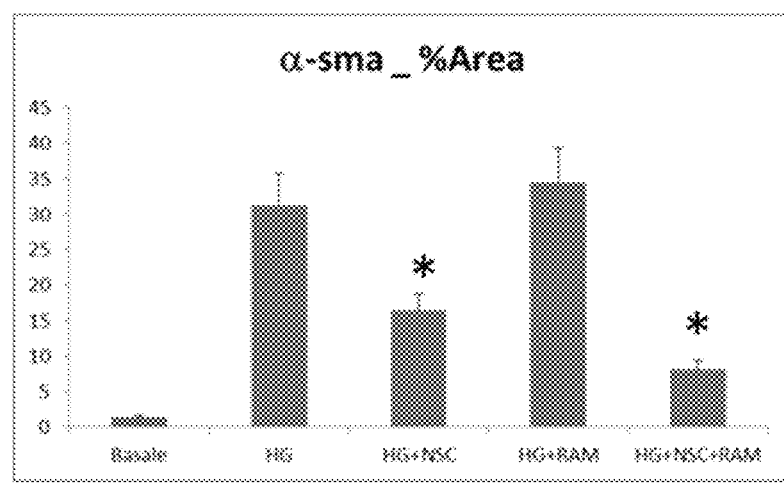

FIG. 5. Quantization of α-sma expression evaluated by confocal microscopy on immortalized renal tubular cells (HK2) under high glucose conditions (HG) in the presence of NSC697923 (NSC), Ramipril (Ram) alone or in combination. Quantification is reported as signal intensity on percentage of Area. *p<0.05 vs HG FIG. 6. NSC697923 (NSC) effect alone or in combination with Ramipril, on lysine 63 ubiquitinated proteins accumulation (Lys63-Ub) and on tubular-interstitial fibrosis (assessed by Sirius red fast green staining) in diabetic mice kidneys (STZ). Letters and numbers in the figure indicate animals represented in the figure. Quantification is reported as a number of strongly positive cells (NSP: number of strong positive cells) compared to the total number of cells (NT).

Figure 7:
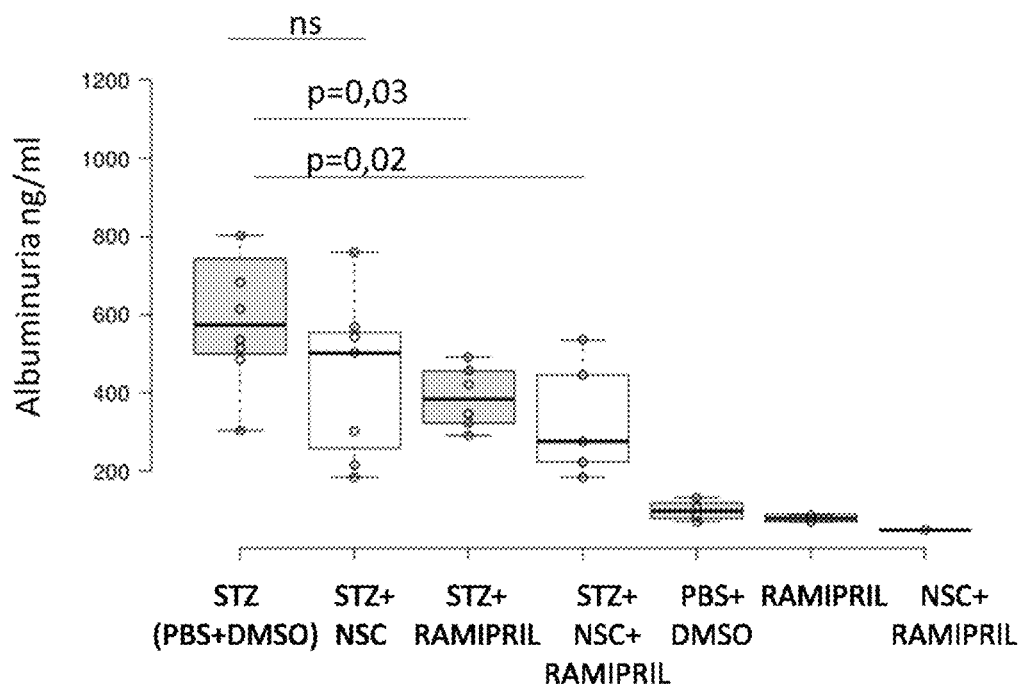

FIG. 7. Urinary albuminuria evaluated by ELISA in diabetic mice (STZ) and controls, treated with drug diluents (PBS+DMSO), NSC697923 (NSC), Ramipril alone or in combination with NSC697923 (NSC+RAMIPRIL).

Figure 8:
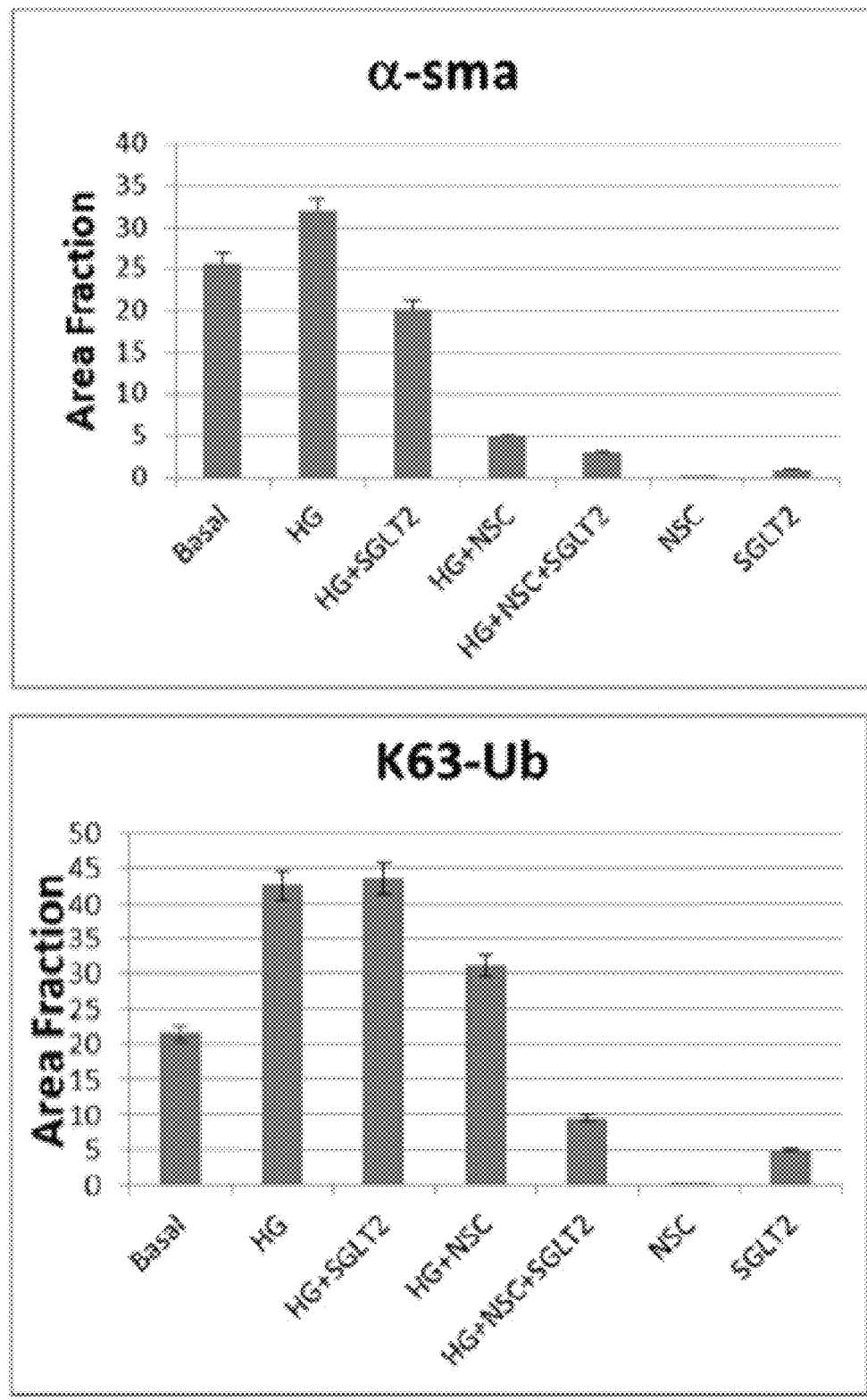

FIG. 8. Quantization of α-sma expression (a) and Lysine 63 ubiquitinated proteins (b) evaluated by confocal microscopy on immortalized renal tubular cells (HK2) in the presence of high glucose (HG), Empaglifozin (SGLT2i), NSC697923 (NSC), alone or in combination. Quantification is reported as signal intensity on percentage of Area.

According to the present invention, the composition of the invention comprises at least one inhibitor of the ubiquitin conjugating enzyme complex (E2) Ubc13/Uev1a.

Inhibitors of the ubiquitin conjugating enzyme complex (E2) Ubc13/Uev1a are known in the field and are commercially available.

Any compound capable of inhibiting the ubiquitin conjugating enzyme complex (E2) Ubc13/Uev1a can be used in the composition of the invention.

The state of the art provides the necessary means and knowledge for an expert in the field to determine if a compound is able to inhibit the ubiquitin conjugating enzyme complex (E2) Ubc13/Uev1a. For example, the ability of a molecule to inhibit this complex can be evaluated by the common western blotting technique, for example evaluating the effect of a molecule considered inhibitor on the expression of UBC13 and Uev1a proteins compared to a control without inhibitor. To this purpose, refer to the work of Pulvino et al., Blood, 2012. Reference can also be made to the work of Scheper J, et al. on PLoS One 2010, where is described a test for the identification of Ubc13/Uev1a complex inhibitors. Therefore, the field expert is quite capable of knowing which compounds can be used in the present invention.

In a preferred embodiment, said inhibitor is the compound 2-(4-methylphenyl) sulfonyl-5-nitrofuran, known as NSC697923. Said compound NSC697923 is commercially available, for example it can be purchased from Selleckem.com, Tocris Bioscience, Calbiochem, Sigma-Aldrich.

Other inhibitors similar to NSC697923 which can be used in the present invention are the compounds described in document WO2013123320 or structurally similar compounds or derived thereof having functional groups that can be combined.

Wherein compounds structurally similar to NSC697923 or derived thereof having functional groups which can be conjugated, wherein functional groups which can be conjugated mean carboxyl groups, alcohol groups, amino groups or other functional group able to form chemically and/or enzymatically hydrolysable covalent bonds.

In another embodiment, said inhibitor is an ubiquitin conjugating enzyme E2 R1 inhibitor (Ubiquitin-conjugating enzyme E2 R1). The inhibitors of said protein are known in the field. For example the molecule known as CC0651 (Cell. 2011 Jun. 24; 145(7):1075-87. An allosteric inhibitor of the human Cdc34 ubiquitin-conjugating enzyme. Ceccarelli DF1, Tang X, Pelletier B, Orlicky S, Xie W, Plantevin V, Neculai D, Chou Y C, Ogunjimi A, AI-Hakim A, Varelas X, Koszela J, Wasney G A, Vedadi M, Dhe-Paganon S, Cox S, Xu S, Lopez-Girona A, Mercurio F, Wrana J, Durocher D, Meloche S, Webb D R, Tyers M, Sicheri F.).

In another embodiment, said inhibitor is the compound known as BAY 11-7082 ((E)-3-(4-Methylphenylsulfonyl)-2-propenenitrle), known to prevent the formation of lysine63-linked poly ubiquitin chains and poly ubiquitinated linear chains (Strickson S, et al. Biochem J. 451(3):427-37, 2013). The BAY-11-7082 compound is purchasable from Anbcam, Santa Cruz Biotechnology, Selleckem.com.

In another embodiment, said inhibitor is the compound known as leucettamol A and its known derivatives, for which refer to Tsukamoto S, et al. Bioorg Med Chem Lett. 2008; 18(24):6319-20.

In another embodiment, said inhibitor is a peptide inhibiting the Ubc13-Uev1 interaction by filling the dimerization interface between the two. Peptides of this type are known in the field, in particular refer to the peptides described in Scheper J, et al. PLoS One. 20 2010; 5 (6): e11403.

The composition of the invention further comprises at least one anti-hypertensive agent, in particular an inhibitor of the renin-angiotensin aldosterone system and/or an hypoglycemic agent.

In an embodiment of the invention, it comprises at least one agent with anti-hypertensive action. Any agent known for its antihypertensive activity acting on the renin-angiotensin-aldosterone system may be used in the composition of the invention. In particular, it can be any drug commonly used for the treatment of arterial hypertension. Said drug may also be a composition, i.e. it may contain more active ingredients with an antihypertensive action. Antihypertensive agents and drugs are known in the field.

In a preferred embodiment, it is an inhibitor of the renin-angiotensin-aldosterone system.

Any compound able to inhibit the renin angiotensin aldosterone system (RAAS) can be used in the composition of the invention.

In particular any compound interfering at any level with the renin angiotensin aldosterone system can be used, including the angiotensin II receptor, causing an inhibition of the system.

In particular, any angiotensin II receptor antagonist.

In an even more preferred embodiment, it is an ACE inhibitor.

Any compound that inhibits the angiotensin converting enzyme (ACE) can be used in the composition of the present invention.

Renin-angiotensin-aldosterone (RAAS) and ACE inhibitors are known in the art and commercially available.

For example Said ACE inhibitor can be selected in the group consisting of: fosinopril, captopril, moexipril, lisinopril, enalapril, quinapril, trandolapril, benazepril, lisinopril, perindopril and ramipril.

Preferably it is ramipril.

For example said angiotensin II receptor inhibitor can be selected in the group consisting of: eprosartan, olmesartan, valsartan, losartan, candesartan, azilsartan medoxomil, irbesartan, valsartan, telmisartan.

In an embodiment of the invention, the composition of the present invention comprises at least one agent with hypoglycemic action. Any agent known for its hypoglycemic activity can be used in the composition of the invention. In particular, it can be any drug commonly used to reduce glycaemia. Said drug may also be a composition, i.e. it may contain more active ingredients with hypoglycemic action.

Hypoglycemic agents and drugs are known in the field and commercially available.

In a preferred embodiment, said hypoglycemic agent is selected in the group consisting of: alpha-glucosidase inhibitors, amylin analogues, dipeptidyl peptidase 4 inhibitors, incretin mimetics, insulin, meglitinides, non-sulfonylureas, SGLT2 inhibitors, sulfonylureas, thiazolidinediones and combinations thereof. All said compounds and classes of compounds are known in the art and commonly used in diabetes therapy.

For example said drug can be selected in the group consisting of: alpha-glucosidase inhibitors (for example miglitol, agarbose), amylin analogues (for example pramlintide), dipeptidyl peptidase 4 inhibitors (for example saxagliptin, sitagliptin, alogliptin, linagliptin), incretin mimetics (eg liraglutide, exenatide, dulaglutide, albiglutide, lixisenatide, semaglutide), insulin (eg insulin, insulin aspart/insulin aspart protamine, insulin lispro/insulin lispro protamine, insulin aspart/insulin aspart protamine, insulin isophane/insulin regular, insulin glulisine, fast-acting insulin, insulin isophane, insulin aspart, insulin lispro, insulin glargine, insulin detemir, insulin degludec, insulin zinc), meglitinides (eg repaglinide, nateglinide), non-sulphonylurea (eg metformin), SGLT2 inhibitors (eg ertugliflozin, empagliflozin, canagliflozin, dapagliflozin), sulfonylureas (eg chlorpropamide, glimepiride, glyburide, glipizide, tolazamide, tolbutamide), thiazolidinediones (eg rosiglitazone, pioglitazone), combinations of antidiabetics drug, or drugs including one or more active ingredients commonly used in diabetes therapy (eg metformin/pioglitazone, glimepiride/pioglitazone, empagliflozin/metformin, dapagliflozin/metformin, glimepiride/rosiglitazone, glyburide/metformin, linagliptin/metformin, linagliptin/metformin, empagliflozin/linagliptin, metformin/sitagliptin, metformin/pioglitazone, metformin/rosiglitazone, metformin/saxagliptin, insulin glargine/lixisenatide, canaglifozin/metformin, alogliptin/metformin, canaglifozin/metformin, metformin/sitagliptin, simvastatin/sitagliptin, glipizide/metformin, alogliptin/pioglitazone, metformin/repaglinide, dapaglifozin/saxagliptin, ertugliflozin/sitagliptin, emagliflozin/metformin, insulin degludec/liraglutide). All these compounds are known in the field and commercially available.

The composition described above can be used as a medicament.

Preferably, it is for the use in the prevention of renal fibrosis, in particular for the prevention of the progression of renal fibrosis.

In fact, the composition of the invention makes it possible to avoid or reduce the appearance of tubulo-interstitial fibrosis that can occur within the kidney under hyperglycemic conditions, thus preventing the development and/or progression of fibrosis.

In one embodiment, it can be used for the early treatment of renal fibrosis.

In fact, said composition can be administered to a patient during the first stages of renal fibrosis in order to treat, block and/or slow the progression of the disease.

Renal fibrosis is a pathological condition that can occur as a result of chronic kidney disease, for example in diabetic nephropathy.

Therefore, the composition of the invention can be used in a patient with any chronic kidney disease for the purpose preventing the onset of fibrosis. In particular, the composition may be for use in a patient with diabetic nephropathy.

In one embodiment, the invention is therefore for the use in the prevention of renal fibrosis resulting from diabetic nephropathy.

The composition can also be used for treatment, in particularly early treatment, of diabetic nephropathy or other renal dysfunctions, for example in order to slow down or prevent the onset of the fibrotic damage.

In this case, the composition is typically administered in the early stages of the disease.

Early-stage renal dysfunction can be identified by an expert in the field through his common knowledge. For example, it can be identified by the appearance in the patient of micro or macro-albuminuria in urine.

In one embodiment, treated subjects are patients affected by diabetes, in particular type 2 diabetes.

More specifically, treated subjects may be diabetic patients with albuminuria.

The composition can be administered to a subject in need thereof by conventional methods.

Conveniently, said medicament is in the form of a preparation for oral administration, but other forms are equally suitable to perform the present invention, for example the parenteral route.

The person expert in the field may decide to administer the composition by any conventional and unconventional pharmaceutical form. Referring to the latest edition of Remington's Pharmaceutical Sciences.

The expert in the field will decide the effective timing of administration, depending on the patient's condition, the severity of the disease, the patient's response and any other clinical parameter included in the general knowledge of this topic.

It is also an object of the present invention a pharmaceutical composition comprising as active ingredients at least one inhibitor of the ubiquitin conjugating enzyme complex Ubc13/Uev1a and at least one antihypertensive agent inhibitor of the renin-angiotensin aldosterone system and/or at least one hypoglycemic agent together with at least one carrier and/or excipient of pharmaceutical grade or compatible with the administration route and pharmaceutically acceptable.

Said composition contains, along with the active ingredients, at least one carrier or an excipient compatible with the route of administration and pharmaceutically acceptable.

Said vector can be a nanoparticle structure, like micelles, liposomes, nanoparticles, nanocapsules, dendrimers, polymeric conjugates, a microparticle, a microcapsule, a macromolecule of natural origin, semi-synthetic and synthetic origin, such as proteins, polysaccharides, poly-lactic acids, poly-glycolic acids, polymeric amino acids, amino acids copolymers, an antibody, a lipid molecule, a phospholipid, an amphiphilic molecule, an inactive viral particle or any other vector known in the pharmaceutical field.

An extensive discussion of commercially available vehicles can be found in the Remington's Pharmaceutical Sciences manual (Mack Pub. Co., N.J. 1991).

Vehicles may additionally contain liquids such as water, saline solution, glycerol and ethanol and other co-solvents.

For example the co-solvents can be: propylene glycol, PEG with different molecular weights, or any other liquid capable of solubilizing the conveyed active ingredients.

In addition, the formulation composition may contain particularly useful adjuvants such as solubilizing agents, complexing agents such as cyclodextrins, dispersing agents, viscosifying agents, suspending agents, emulsifying agents, sweetening and flavoring agents.

Said components allow to formulate the solid, semisolid and liquid pharmaceutical compositions, such as tablets, pills, capsules, sugar-coated pills, liquids, gels, syrups, doughs, suspensions and similar, for example for oral administration.

All said components are known in the field and can be easily chosen by the expert based on his general knowledge in the pharmaceutical field Once formulated, the composition can be administered directly to the subject. The subjects to be treated can be animals; in particular, they can be human subjects.

The medicament of the invention can be administered by any route, including the oral, intravenous, intramuscular, intra-arterial, intramedullary, intrathecal, intraventricular, transdermal or transcutaneous, subcutaneous, intraperitoneal, intranasal, enteral, topical, sublingual intravaginal or rectal. A preferred route is the oral route.

The compositions for oral administration can be in the form of liquid solutions or liquid suspensions or liquid emulsions or powders. Most commonly, they are in a unit dosage form to facilitate the dosage. A unit dosage form means a discrete unit suitable as a unit dose for human subjects and other mammals, each unit containing a predetermined amount of active ingredient calculated to produce the desired therapeutic effect, in association with a pharmaceutically acceptable excipient. Typical unit dosage forms include ampoules or pre-measured syringes for liquid compositions or pills, tablets, capsules or similar in the case of solid compositions. In said compositions, the compounds of the invention are generally a minor component (for example from about 0.1 to about 50% by weight or preferably from about 1 to about 40% by weight), the leftovers comprises various vehicles or vectors and auxiliaries substances useful to compose the desired dosage form. The treatment may include a single dose or multiple dose administration.

The pharmaceutical compositions according to the present invention can also contain one or more further active ingredients.

Said additional active ingredient may be, for example, a compound known for use in diabetic nephropathy.

The medium amount of active compound may vary and in particular should be based on the recommendations and prescription of a qualified doctor. The administration regimen, dosage and posology will be decided by the doctor based on his experience, on the illness to be treated and on the patient's condition and on the general knowledge in the field.

For each compound, the therapeutically effective dose can be estimated initially in cell culture assays or in animal models, generally mice, rats, guinea pigs, dogs or pigs. The animal model can also be used to determine the appropriate concentration range and route of administration. This information can be used to define doses and administration routes useful for humans. To calculate the Human Equivalent Dose (HED) we recommend using the conversion table provided in the Guidance for Industry and Reviewers (2002, U.S. Food and Drug Administration, Rockville, Maryland, USA).

A mean dose for human administration may be established during clinical trials, as is usual in the industry.

The specific effective dose for a human subject will then depend on the severity of the disease, the general health state of the subject, age, weight and sex of the subject, diet, time and frequency of administration, any combinations of drugs and the tolerance/response to therapy. Said quantity can be determined by routine experimentation and is part of the physician's evaluation.

Depending on the chosen route of administration, the compositions will be in solid, semi-solid or liquid form, suitable for oral or parenteral administration or any other type of chosen administration.

In an embodiment of the invention, the pharmaceutical composition of the invention is for use as a medicament. Preferably, it is for use in the prevention of renal fibrosis or for the other uses as described above.

The composition of the invention can also be in the form of a kit comprising as component a) an inhibitor of the ubiquitin conjugating enzyme complex Ubc13/Uev1a and as component b) an anti-hypertensive agent, such as inhibitors of the renin angiotensin-aldosterone system, and/or a hypoglycemic agent or combinations thereof. In this case, the two components a) and b) can be administered simultaneously or in any succession.

An object of the present invention is also an inhibitor of the ubiquitin conjugating enzyme complex Ubc13/Uev1a for use in the prevention of renal fibrosis in combined therapy with at least one antihypertensive agent and/or at least one hypoglycemic agent or in a therapeutic regimen containing at least one antihypertensive agent and/or a combination of drugs commonly used in diabetes therapy. A therapeutic regimen consisting of a combination of drugs commonly used in diabetes therapy means a therapy that involves the simultaneous use of two or more drugs commonly used in the treatment of diabetes, for example an association of antihypertensive drugs with hypoglycemic drugs or other antidiabetic drugs. The compounds can then be administered to a subject through a single composition comprising all the active ingredients or through separate compositions, one for each active ingredient, administered simultaneously or sequentially, in any order. The expert in the field will be able to choose the most appropriate therapy, times and dosages by referring to his general knowledge in the field.

The invention will now be further illustrated by the following examples.

EXAMPLES

Materials and Methods

Cell Cultures

HK2 cells, a line of Renal Proximal Tubule Epithelial Cells (PTEC) obtained from a human control kidney, were purchased from the American Type Culture Collection (ATCC, Rockville, MD). Cells were cultured in DMEM growth medium low glucose (5.5 mM) with the addition of 10% fetal bovine serum (FBS), 1% Penicillin and Streptomycin and 1% L-Glutamine (Sigma-Aldrich, Munich, Germany). Prior to each passage, cells reaching confluence were rinsed with phosphate-buffered saline (PBS), trypsinized with Trypsin 0.05% and Ethylenediaminetetraacetic acid (EDTA) 0.02% in PBS and seeded in complete growth medium with or without the addition of D-Glucose 24.5 mM (final concentration in hyperglycemia HG=30 mM) or L-Glucose 24.5 mM as osmolarity control, for each predetermined time point. Cells were then incubated at 37° C. in 5% CO2.

Western Blotting

Cells were plated in six-well plates and incubated to reach confluence. Cells were then exposed to either D- or L-Glucose at a concentration of 30 mM for the indicated time point. Prior to the addition of glucose, cells were pre-incubated with the specific inhibitor of Lysine63-linked ubiquitylation, NSC697923, at a 1 µM final concentration, and with the ACE-inhibitor Ramipril at a final concentration of 10 µM. Following incubation cells were lysed in 100 µL RIPA Buffer (containing 5 mM EDTA, 1 mM Sodium orthovanadate, 150 mM sodium chloride, 1.5% Nonidet P-40, 20 mM Tris-HCl pH 7.4, 2-chloroacetamide 10 µl/ml, phosphatase inhibitors 10 µl/ml). The lysate was then incubated in ice 30 min and subsequently centrifuged 5 min at 10.000 g at 4° C. A total amount of 40 µg protein lysate for each condition was then separated using a 4-15% precast polyacrylamide gel (Biorad, Milano, Italia) and transferred onto a PVDF membrane with pore size 0.2 um (Biorad). The membrane was blocked for 30 min using 5% Skim Milk Powder in TPBS (PBS1X+Tween 20 0.1%) and then incubated with the primary antibody anti-α-sma (Santa Cruz). After washing in TPBS, the membrane was incubated for 1 h at ambient temperature with the specific secondary antibody conjugated to horseradish peroxidase (HRP). The enhanced chemiluminescence (ECL) system was used for signal detection (Amersham, Milano, Italia).

Immunofluorescence on HK2 Cells

The cellular distribution of the proteins showing lysine63-linked ubiquitylation and the expression of the mesenchymal marker α-sma was evaluated in HK2 cells through indirect immunofluorescence and confocal microscopy analysis following incubation with specific antibodies. For each condition, 150.000 cells were plated on sterile glass slides and then incubated with D- or L-Glucose 30 mM for the indicated time point. In some predetermined conditions, the specific inhibitor of Lysine63-linked ubiquitylation, NSC697923, was pre-incubated at a 1 μM final concentration, 1 h prior to the addition of glucose and/or the ACE-inhibitor Ramipril at a final concentration of 10 μM and/or the SGLT2 inhibitor Empaglifozin at a 500 nM final concentration. Following stimulation, HK2 were fixed 15 min in paraformaldehyde 4%, treated 5 min with Triton-X 100 0.1% in PBS, and incubated 1 h in blocking buffer (goat serum 4%+BSA 2%). Cells were then incubated 1 h with the specific antibodies against α-sma and lysine63 ubiquitin diluted in blocking buffer. The antigen-antibody complex was then identified using a secondary fluorescent antibody (specifically Alexa Fluor 555 goat anti-rabbit and Alexa Fluor 488 goat anti-mouse). Prior to the incubation with the secondary antibody, cells were rinsed three times in PBS. Cells nuclei were then stained using TO-PRO-3 diluted in PBS and slides were mounted. The negative control was obtained incubating cells in blocking without the addition of the primary antibody. The fluorescence signal was then acquired using the Leica TCS SP2 confocal microscope and images were saved at a 63× zoom using the microscope software. Signal was finally quantified measuring the area % of fluorescent signal compared to the background.

Immunohistochemistry on Tissue

Tissue samples were obtained from kidney of DBA/2J mice. Following sacrifice, tissues were fixed in 4% formaldehyde. In order to evaluate the accumulation of proteins undergoing Lysisine63-linked ubiquitylation through immunohistochemistry, dewaxed and unmasked sections were incubated 10 min in H2O2 and 5 min in Triton 0.25% at ambient temperature. Sections were then blocked 10 min with Protein block (Dako, Glostrup, Denmark) and then incubated 1 h with the specific antibody against and lysine63-linked ubiquitylation. Signal was revealed using the Dako EnVision G2 System (Dako). Sections were stained with hematoxylin and slides were mounted with glycerol. The negative control sample lacks the primary antibody incubation step. The signal is then quantified using the Positive Pixel Count v9_v10.0.0.1805 algorithm (Aperio Technologies) that measures the number of positive cells on the total number of cells.

Sirius Red Staining

Tissue samples were obtained from kidneys of DBA/2J mice following sacrifice. Tissue was fixed in 4% formaldehyde. Following dewaxing and hydration, sections were incubated with Bouin's solution overnight at ambient temperature. Sections were then rinsed using running tap water to remove all the fixative residues and incubated 1 h at ambient temperature with the Sirius Red/Fast Green dye combination 1:1.

Animal Model

The animal model employed is the murine model DBA/2J. 8-weeks-old mice received daily intraperitoneal injections for five consecutive days of either sodium citrate (females, control group) or streptozotocin (STZ, 45 mg/kg, pH4.5, dissolved in sodium citrate) for the study group (males). Only those animals showing a blood glucose level above 250 mg/dl were included in this study. Five weeks following the last STZ injection, animals were treated with NSC697923 dissolved in PBS (3 mg/kg, 3 times a week for 6 weeks) and/or RAMIPRIL (2 mg/kg, 3 times a week for 6 weeks) dissolved in DMSO 2% either alone or in combination [NSC697923 (3 mg/kg)+RAMIPRIL (2 mg/kg) 3 times a week for 6 weeks]. Serum and 24 h urine samples were collected at the end of the treatment. Kidney samples were collected at sacrifice and immediately fixed in formalin and embedded in paraffin.

Urinary Albumin Analysis

Urinary albumin concentration was measured in the urine of these animals using the commercially available Mouse Albumin ELISA Kit (Abcam). The urinary albumin values were normalized to the total urinary protein content compared to the total volume of urines produced during the 24 h before sacrifice.

Example 1

NSC697923 Reduces Lysine 63 Ubiquitinated Proteins Accumulation (Lys63-Ub) and Tubular-Interstitial Fibrosis in Diabetic Mice (STZ)

Lysine 63 ubiquitinated proteins accumulation has been evaluated by immunohistochemistry on renal tissues from the mice model of diabetic nephropathy (DBA/2J mice+streptozotocin-STZ); the degree of fibrosis in these samples has been evaluated by Sirius Red Fast Green staining.

Results are reported in FIGS. 1 and 2.

Diabetic mice (STZ) show high accumulation of lysine 63 ubiquitinated proteins and a high degree of fibrosis; treatment with NSC697923 significantly reduces both processes. These data support the use of the NSC697923 inhibitor to prevent the renal damage and tubular interstitial fibrosis in diabetic patients.

Example 2

NSC697923 does not Reduce Albuminuria in Diabetic Mice In Vivo

The analysis of the clinical data of the mice under study showed that NSC697923 has no effect on urinary albuminuria in treated diabetic mice (STZ+NSC697923) compared to untreated diabetic mice (STZ). The results are shown in the following Table 1.

TABLE 1

| | Animals number | Weight at Sacrifice | Kidney Weight | Blood glucose at sacrifice | Urinary Volume (mL/24 h) | ug urine albumin 24 h |
|---|---|---|---|---|---|---|
| CTRL | 13 | 21.379 ± 3.15 | 0.4 ± 0.15 | 123.76 ± 0.15 | 0.4 ± 0.21 | 16.17 ± 9.8 |
| NSC697923 | 6 | 18.37 ± 0.67 | 0.24 ± 0.018 | 118.8 ± 10.44 | 0.33 ± 0.17 | |
| STZ | 21 | 16.75 ± 1.92 | 0.38 ± 0.043 | 477.31 ± 138.83 | 24.14 ± 1.9 | 561.29 ± 390.56 |
| STZ + NSC697923 | 6 | 18.08 ± 0.59 | 0.33 ± 0.079 | 540.5 ± 33.05 | 25.83 ± 12.58 | 724.25 ± 690.89 |

Albuminuria first and proteinuria later, can have a direct role in the progression of chronic kidney disease since they can induce a tubular-interstitial damage.

Example 3

NSC697923, Alone and in Combination with ACE-Inhibitors, Reduces the Hyperglycemia-Induced Epithelial-to-Mesenchymal Transition By western blotting on cultured immortalized renal tubular cells (HK2) we evaluated the protein expression levels of α-sma, a marker of epithelial-to-mesenchymal transition.

Results are reported in FIG. 3.

Hyperglycemia induces α-sma expression, that is reduced by the NSC697923. ACE-inhibitors alone, instead, have no effect on the hyperglycemia-induced epithelial-to-mesenchymal transition (and then on α-sma expression), while α-sma expression, in association with NSC697923, is under basal levels (see the graph at FIG. 3).

Example 4

Hyperglycemia-Induced Accumulation of Lysine 63 Ubiquitinated Proteins and α-Sma Expression, are Reduced by NSC697923 and not by ACE Inhibitors.

We evaluated the α-sma expression and the accumulation of lysine 63 ubiquitinated proteins by immunofluorescence and confocal microscopy on HK2 cells under hyperglycemic conditions and in the presence of ACE inhibitors or NSC697923.

Figure 4:
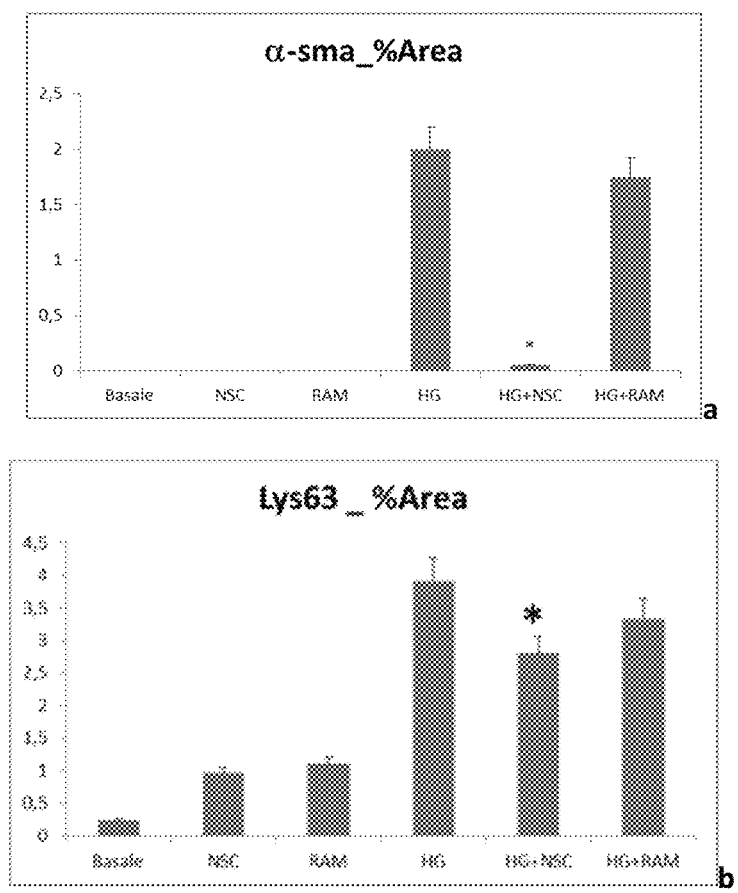

As demonstrated in FIG. 4, ACE inhibitors do not block α-sma expression (a) and do not reduce the hyperglycemia-induced accumulation of lysine 63 ubiquitinated proteins (b); otherwise NSC697923 reduces both processes.

Example 5

The Combination of NSC697923 and ACE Inhibitors Further Reduce the Epithelial-to Mesenchymal Transition.

We evaluated the α-sma expression by immunofluorescence and confocal microscopy on HK2 cells under hyperglycemic conditions and in the presence of ACE inhibitors and NSC697923, alone or in combination.

Results are reported in FIG. 5.

As previously demonstrated, ACE inhibitors alone do not reduce hyperglycemia-induced α-sma expression. We confirmed once again that the NSC697923 inhibitor alone is able to inhibit hyperglycemia-induced □-sma expression and the combination of both molecules further reduces the epithelial-to-mesenchymal transition. On the contrary, ACE inhibitors alone do not block this process.

Example 6

The Combination of NSC697923 and ACE Inhibitors Reduces the Accumulation of Lysine 63 Ubiquitinated Proteins and the Tubular Interstitial Fibrosis In Vivo in Diabetic Mice.

We evaluated the accumulation of lysine 63 ubiquitinated proteins by immunohistochemistry and the degree of fibrosis by Sirius Red Fast Green staining on renal tissue of diabetic mice (STZ) undergoing a single or combined treatment with NSC697923 and/or ACE inhibitors.

Figure 6:
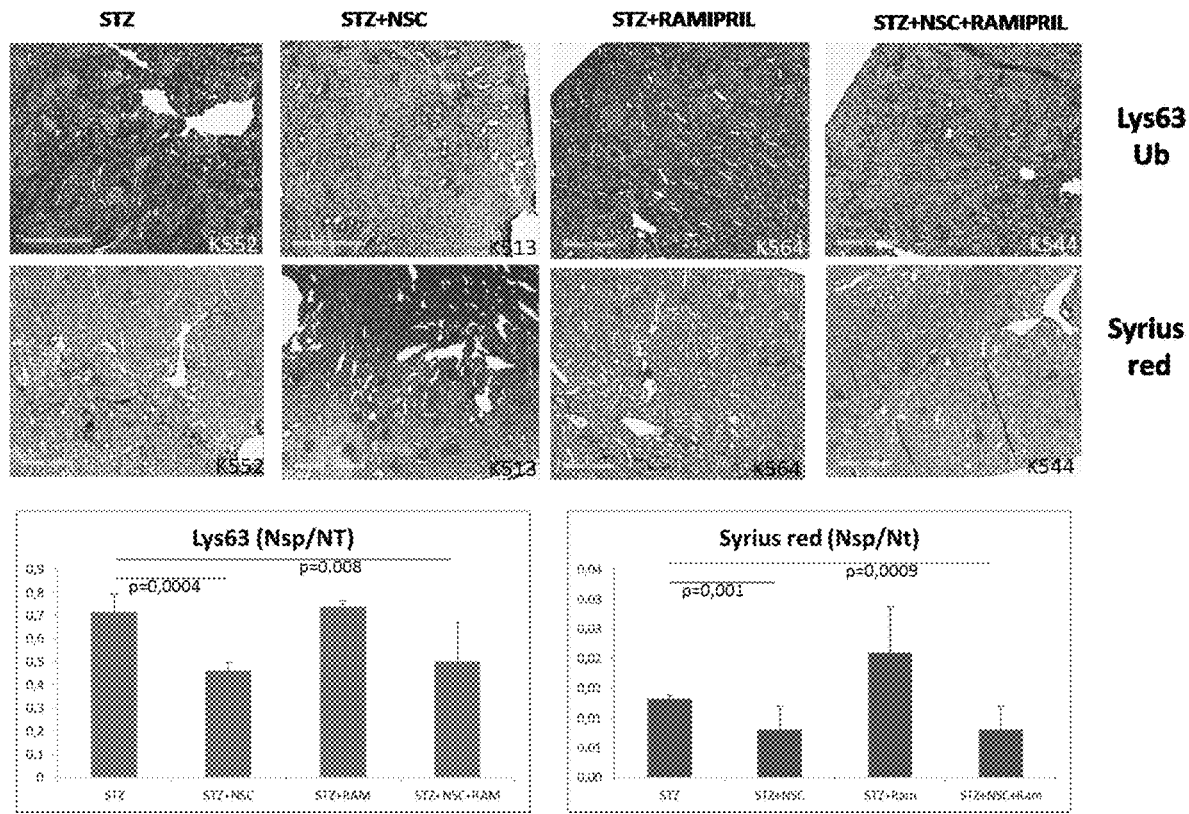

As shown in FIG. 6, diabetic mice STZ treated with NSC697923 alone or in combination with ACE inhibitors, present a significant reduction in the accumulation of lysine 63 ubiquitinated proteins and in the degree of fibrosis when compared to untreated diabetic mice or mice treated with ACE inhibitors alone.

Example 7

Effect of the Combination of NSC697923+ACE Inhibitors on Albuminuria in Diabetic Mice In Vivo.

The first stage of development of diabetic nephropathy is characterized by the appearance of microalbuminuria that, without an effective treatment, leads in the 20-40% of diabetic patients to a complete loss of renal function. In the first group of animals we observed that the NSC697923 compound alone, was not able to reduce albuminuria although capable of reducing tubular interstitial fibrosis. Therefore in a new animal group we evaluated the effect on albuminuria of the combination NSC697923+ACE inhibitors in diabetic mice in vivo.

Analyzing the clinical data of mice under study, we observed that the combination of NSC697923 with ACE inhibitor, significantly reduces albuminuria in diabetic mice (STZ), both compared to untreated mice and compared to diabetic mice treated only with NSC697923, with a trend of further reduction of albuminuria also compared to diabetic mice treated only with ramipril.

Results are reported in the following Table 2 and in FIG. 7.

TABLE 2

|  | Animals number | Weight at Sacrifice | Kidney Weight | Blood glucose at sacrifice | Urinary Volume (mL/24 h) | ug urine albumin 24 h |
|---|---|---|---|---|---|---|
| CTRL PBS | 5 | 19.7 ± 1.39 | 0.232 ± 0.035 | 119.8 ± 11.39 | (0.265 ± 0.23) $10^{-3}$ | 120.18 ± 17.49 |
| CTRL DMSO | 5 | 20.07 ± 2.05 | 0.232 ± 0.04 | 114.8 ± 15.51 | (0.525 ± 0.24) $10^{-3}$ | 78.87 ± 12.16 |
| RAMIPRIL | 5 | 19.96 ± 1.25 | 0.242 ± 0.027 | 112 ± 9.14 | (0.71 ± 0.41) $10^{-3}$ | 128.54 ± 55.94 |
| NSC697923 + RAMIPRIL | 5 | 21.38 ± 1.02 | 0.272 ± 0.029 | 115.2 ± 9.36 | 0.61 ± $10^{-3}$ (1 result available) | 50.28 |
| STZ (PBS) | 4 | 17.38 ± 1.48 | 0.377 ± 0.076 | 554.5 ± 53.77 | 31.87 ± 6.57 | 577.98 ± 92.04 |
| STZ (DMSO) | 4 | 16.89 ± 1.37 | 0.39 ± 0.055 | 587.25 ± 25.5 | 26.62 ± 6.3 | 551.76 ± 209.81 |
| STZ + NSC697923 | 7 | 16.54 ± 1.59 | 0.38 ± 0.05 | 594.28 ± 7.95 | 24.85 ± 7.78 | 439.29 ± 211.2 |
| STZ + RAMIPRIL | 7 | 16.24 ± 1.43 | 0.37 ± 0.054 | 555.71 ± 71.48 | 29.64 ± 9.51 | 388.79 ± 79.78 |
| STZ + NSC697923 + RAMIPRIL | 6 | 15.51 ± 1.8 | 0.35 ± 0.039 | 554.5 ± 53.81 | 25.83 ± 8.6 | 333.67 ± 150.82 |

Example 8

Effect of the Combination of NSC697923+SGLT2 Inhibitors on Human Renal Tubular Cells HK2

We evaluated the α-sma expression and the accumulation of lysine 63 ubiquitinated proteins by immunofluorescence and confocal microscopy on HK2 cells under hyperglycemic conditions (HG) and in the presence of empaglifozin (SGLT2 inhibitor) or NSC697923 and their association.

The obtained results are shown in FIG. 8 and demonstrate that SGLT2 receptor inhibitors do not reduce accumulation of lysine 63 ubiquitinated proteins under hyperglycemic conditions and partially reduce hyperglycemia induced α-sma expression; NSC697923 on the other hand reduces both processes. The association between NSC697923 and SGLT2 inhibitors has a synergic and significantly evident effect on the reduction of both processes.

The invention claimed is:

1. A method for treating or preventing the progression of renal fibrosis comprising administration to an individual in need thereof a pharmaceutical composition of comprising:
   (a) at least one inhibitor of a ubiquitin conjugating enzymatic complex Ubc13/Uev1a comprising 2-(4-methylphenyl) sulfonyl-5-nitrofuran; and
   (b) at least one antihypertensive agent inhibiting the renin-angiotensin-aldosterone system comprising ramipril.

2. The method of claim 1, wherein said renal fibrosis is consequent to diabetic nephropathy.

3. The method of claim 1, wherein the pharmaceutical composition further comprises at least one hypoglycemic agent comprising empagliflozin.

4. A method for treating or preventing the progression of diabetic nephropathy comprising administration to an individual in need thereof a pharmaceutical composition comprising:
   (a) at least one inhibitor of a ubiquitin conjugating enzymatic complex Ubc13/Uev1a comprising 2-(4-methylphenyl) sulfonyl-5-nitrofuran; and
   (b) at least one antihypertensive agent inhibiting the renin-angiotensin-aldosterone system comprising ramipril.

5. The method of claim 4, wherein the individual in need thereof is a diabetic patient.

6. The method of claim 5, wherein said patient is suffering from diabetic nephropathy.

7. The method of claim 4, wherein the pharmaceutical composition further comprises at least one hypoglycemic agent comprising empagliflozin.

8. A method for treating or preventing the progression of renal fibrosis comprising administration to an individual in need thereof:
   (a) at least one inhibitor of a ubiquitin conjugating enzymatic complex Ubc13/Uev1a comprising 2-(4-methylphenyl) sulfonyl-5-nitrofuran; and
   (b) at least one antihypertensive agent inhibiting the renin-angiotensin-aldosterone system comprising ramipril.

9. The method of claim 8, wherein said renal fibrosis is consequent to diabetic nephropathy.

10. The method of claim 8, further comprising administering to the individual in need thereof at least one hypoglycemic agent comprising empagliflozin.

11. A method for treating or preventing the progression of diabetic nephropathy comprising administration to an individual in need thereof:
   (a) at least one inhibitor of a ubiquitin conjugating enzymatic complex Ubc13/Uev1a comprising 2-(4-methylphenyl) sulfonyl-5-nitrofuran; and
   (b) at least one antihypertensive agent inhibiting the renin-angiotensin-aldosterone system comprising ramipril.

12. The method of claim 11, wherein the individual in need thereof is a diabetic patient.

13. The method of claim 12, wherein said patient is suffering from diabetic nephropathy.

14. The method of claim 11, further comprising administering to the individual in need thereof at least one hypoglycemic agent comprising empagliflozin.

15. A method for treating, preventing, or preventing the progression of renal fibrosis comprising administration to an individual in need thereof:
   (a) at least one inhibitor of a ubiquitin conjugating enzymatic complex Ubc13/Uev1a comprising 2-(4-methylphenyl) sulfonyl-5-nitrofuran; and
   (b) at least one hypoglycemic agent comprising empagliflozin.

16. The method of claim 15, wherein said renal fibrosis is consequent to diabetic nephropathy.

17. A method for treating, preventing, or preventing the progression of diabetic nephropathy comprising administration to an individual in need thereof:
   (a) at least one inhibitor of a ubiquitin conjugating enzymatic complex Ubc13/Uev1a comprising 2-(4-methylphenyl) sulfonyl-5-nitrofuran; and
   (b) at least one hypoglycemic agent comprising empagliflozin.

18. The method of claim 17, wherein the individual in need thereof is a diabetic patient.

19. The method of claim 18, wherein said patient is suffering from diabetic nephropathy.

* * * * *